(12) United States Patent
Fernando (10) Patent No.: US 11,753,682 B2
(45) Date of Patent: Sep. 12, 2023

(54) NONINVASIVE MOLECULAR CONTROLS (71) Applicant: Father Flanagan's Boys' Home, Omaha, NE (US)

(72) Inventor: M. Rohan Fernando, Omaha, NE (US)

(73) Assignee: Father Flanagan's Boys'Home, Omaha, NE (US)

( * ) Notice: Subject to any disclaimer, the term of this patent is extended or adjusted under 35 U.S.C. 154(b) by 1287 days.

(21) Appl. No.: 16/082,107

(22) PCT Filed: Mar. 6, 2017

(86) PCT No.: PCT/US2017/020987
§ 371 (c)(1),
(2) Date: Sep. 4, 2018

(87) PCT Pub. No.: WO2017/155894
PCT Pub. Date: Sep. 14, 2017

(65) Prior Publication Data
US 2020/0283846 A1  Sep. 10, 2020

Related U.S. Application Data (60) Provisional application No. 62/304,712, filed on Mar. 7, 2016.

(51) Int. Cl.
*C12Q 1/6876* (2018.01)
*C12Q 1/6834* (2018.01)

(52) U.S. Cl.
CPC ......... *C12Q 1/6876* (2013.01); *C12Q 1/6834* (2013.01); *C12Q 2600/154* (2013.01); *C12Q 2600/158* (2013.01); *G01N 2333/471* (2013.01); *G01N 2333/82* (2013.01); *G01N 2800/368* (2013.01); *G01N 2800/387* (2013.01)

(58) Field of Classification Search
CPC . Y10T 436/10; C12N 15/10; C12Q 2545/113; C12Q 2537/16; C12Q 2600/166
See application file for complete search history.

(56) References Cited

U.S. PATENT DOCUMENTS

| | | | |
|---|---|---|---|
| 5,108,746 A | 4/1992 | Rho et al. | |
| 5,449,604 A | 9/1995 | Schellenberg | |
| 6,015,662 A | 1/2000 | Hackett, Jr. et al. | |
| 6,177,278 B1 | 1/2001 | Haj-Ahmad | |
| 6,221,654 B1 | 4/2001 | Quake et al. | |
| 6,291,248 B1 | 9/2001 | Haj-Ahmad | |
| 6,344,325 B1 | 2/2002 | Quake et al. | |
| 6,818,395 B1 | 11/2004 | Quake et al. | |
| 6,911,345 B2 | 6/2005 | Quake et al. | |
| 6,964,736 B2 | 11/2005 | Quake et al. | |
| 7,026,453 B2 | 4/2006 | Haj-Ahmad | |
| 7,216,671 B2 | 5/2007 | Unger et al. | |
| 7,297,518 B2 | 11/2007 | Quake et al. | |
| 7,368,237 B2 | 5/2008 | Parrish et al. | |
| 7,431,842 B2 | 10/2008 | Haj-Ahmad | |
| 7,501,245 B2 | 3/2009 | Quake et al. | |
| 7,678,547 B2 | 3/2010 | Eyal et al. | |
| 7,700,824 B2 | 4/2010 | Hossain et al. | |
| 7,785,777 B2 | 8/2010 | Rommens et al. | |
| 7,888,017 B2 | 2/2011 | Quake et al. | |
| 7,897,356 B2 | 3/2011 | Klass et al. | |
| 7,981,604 B2 | 7/2011 | Quake | |
| 8,008,018 B2 | 8/2011 | Quake et al. | |
| 8,063,199 B2 | 11/2011 | Haj-Ahmad | |
| 8,076,090 B2 | 12/2011 | Fang et al. | |
| 8,104,497 B2 | 1/2012 | Unger | |
| 8,192,954 B2 | 6/2012 | Klass et al. | |
| 8,207,316 B1 | 6/2012 | Bentwich | |
| 8,211,653 B2 | 7/2012 | Klass et al. | |
| 8,278,059 B2 | 10/2012 | Klass et al. | |
| 8,293,470 B2 | 10/2012 | Quake et al. | |

(Continued)

FOREIGN PATENT DOCUMENTS

| | | |
|---|---|---|
| JP | 2008189567 A | 8/2008 |
| WO | 03018757 A2 | 3/2003 |
| WO | 2009/100029 A1 | 8/2009 |
| WO | 2011/156734 A2 | 12/2011 |
| WO | 2014172447 A1 | 10/2014 |

OTHER PUBLICATIONS

Kenneth W Witwer et al: "Standardization of sample collection, isolation and analysis methods in extracellular vesicle research", Journal of Extracellular Vesicles, vol. 2, May 27, 2013 (May 27, 2013), p. 25pp, XP007923200, ISSN: 2001-3078, DOI: 10.3402/JEV.V2I0.20360 [retrieved on May 27, 2013].

(Continued)

*Primary Examiner* — Joseph G. Dauner
(74) *Attorney, Agent, or Firm* — McKee, Voorhees & Sease, PLC (57) ABSTRACT

A method of making a noninvasive molecular control and analysis is described. The method of making the noninvasive molecular control includes, predetermining a positive control for a condition of interest, selecting a cell line with a control marker for the condition of interest, amplifying release of cfDNA from the selected cell line, isolating the released cfDNA from the selected cell line, quantifying the control marker from the isolated cfDNA, determining a volume of the control marker for addition to an isolated control plasma, isolating the control plasma from a control sample, treating the isolated control plasma with a control stabilizer, determining a volume of the control plasma to add to the volume of control marker, combining the volume of the control marker with the isolated control plasma, and analyzing a sample against the noninvasive molecular control to determine the presence or absence of a condition of interest.

28 Claims, 2 Drawing Sheets

(56) References Cited

U.S. PATENT DOCUMENTS

| | | |
|---|---|---|
| 8,338,116 B2 | 12/2012 | Fang et al. |
| 8,540,985 B2 | 9/2013 | Jensen et al. |
| 8,568,994 B2 | 10/2013 | Altevogt et al. |
| 8,852,876 B2 | 10/2014 | Fang et al. |
| 8,901,284 B2 | 12/2014 | Vlassov et al. |
| 8,999,380 B2 | 4/2015 | Bancel et al. |
| 9,012,135 B2 | 4/2015 | Haj-Ahmad |
| 9,095,552 B2 | 8/2015 | Chakraborty et al. |
| 9,107,886 B2 | 8/2015 | Chakraborty et al. |
| 9,114,113 B2 | 8/2015 | Chakraborty et al. |
| 9,127,312 B2 | 9/2015 | Regan et al. |
| 9,128,101 B2 | 9/2015 | Halbert et al. |
| 9,220,792 B2 | 12/2015 | Chakraborty et al. |
| 9,233,141 B2 | 1/2016 | Chakraborty et al. |
| 2002/0025529 A1 | 2/2002 | Quake et al. |
| 2002/0029814 A1 | 3/2002 | Unger et al. |
| 2002/0053532 A1 | 5/2002 | Quake et al. |
| 2002/0123033 A1 | 9/2002 | Eyal et al. |
| 2002/0164629 A1 | 11/2002 | Quake et al. |
| 2005/0142568 A1 | 6/2005 | Parrish et al. |
| 2005/0147992 A1 | 7/2005 | Quake et al. |
| 2006/0019263 A1 | 1/2006 | Quake et al. |
| 2006/0019267 A1 | 1/2006 | Quake |
| 2006/0046258 A1 | 3/2006 | Lapidus et al. |
| 2006/0056948 A1 | 3/2006 | Hossain et al. |
| 2006/0068405 A1 | 3/2006 | Diber et al. |
| 2006/0110734 A1 | 5/2006 | Rommens et al. |
| 2006/0257903 A1 | 11/2006 | Akil et al. |
| 2007/0054293 A1 | 3/2007 | Liu |
| 2007/0202525 A1 | 8/2007 | Quake et al. |
| 2008/0142445 A1 | 6/2008 | Haj-Ahmad |
| 2008/0225933 A1 | 9/2008 | Chan et al. |
| 2009/0142790 A1 | 6/2009 | Fang et al. |
| 2009/0154591 A1 | 6/2009 | Wong et al. |
| 2009/0170113 A1 | 7/2009 | Quake et al. |
| 2009/0170114 A1 | 7/2009 | Quake et al. |
| 2009/0181421 A1 | 7/2009 | Kapur et al. |
| 2009/0257445 A1 | 10/2009 | Chan et al. |
| 2010/0063266 A1 | 3/2010 | Haj-Ahmad |
| 2010/0090774 A1 | 4/2010 | Shumarayev et al. |
| 2010/0109675 A1 | 5/2010 | Wong et al. |
| 2010/0124751 A1 | 5/2010 | Quake et al. |
| 2010/0124752 A1 | 5/2010 | Quake et al. |
| 2010/0171954 A1 | 7/2010 | Quake et al. |
| 2010/0196426 A1 | 8/2010 | Skog et al. |
| 2010/0197522 A1 | 8/2010 | Liu et al. |
| 2010/0255492 A1 | 10/2010 | Quake et al. |
| 2010/0255493 A1 | 10/2010 | Quake et al. |
| 2010/0256013 A1 | 10/2010 | Quake et al. |
| 2010/0279315 A1 | 11/2010 | Altevogt et al. |
| 2011/0003008 A1 | 1/2011 | Lim |
| 2011/0003704 A1 | 1/2011 | Skog et al. |
| 2011/0053157 A1 | 3/2011 | Skog et al. |
| 2011/0066566 A1 | 3/2011 | Adams et al. |
| 2011/0091454 A1 | 4/2011 | Diber et al. |
| 2011/0118125 A1 | 5/2011 | Maron et al. |
| 2011/0144076 A1 | 6/2011 | Williams et al. |
| 2011/0150775 A1 | 6/2011 | Slonim et al. |
| 2011/0151460 A1 | 6/2011 | Klass et al. |
| 2011/0159506 A1 | 6/2011 | Klass et al. |
| 2011/0224087 A1 | 9/2011 | Quake et al. |
| 2011/0236953 A1 | 9/2011 | Walsh et al. |
| 2011/0237450 A1 | 9/2011 | Klass et al. |
| 2011/0275523 A1 | 11/2011 | Quake |
| 2011/0286993 A1 | 11/2011 | Jensen et al. |
| 2012/0021407 A1 | 1/2012 | Haj-Ahmad |
| 2012/0028342 A1 | 2/2012 | Ismagilov et al. |
| 2012/0053335 A1 | 3/2012 | Liu |
| 2012/0058480 A1 | 3/2012 | Lewis et al. |
| 2012/0071351 A1 | 3/2012 | Fang et al. |
| 2012/0107413 A1 | 5/2012 | Lim et al. |
| 2012/0142001 A1 | 6/2012 | Skog et al. |
| 2012/0156731 A1 | 6/2012 | Huang et al. |
| 2012/0164648 A1 | 6/2012 | Han et al. |
| 2012/0165203 A1 | 6/2012 | Quake et al. |
| 2012/0219632 A1 | 8/2012 | Lim |
| 2012/0222139 A1 | 8/2012 | Hu et al. |
| 2012/0269774 A1 | 10/2012 | Ichim et al. |
| 2012/0280724 A1 | 11/2012 | Chan et al. |
| 2012/0295286 A1 | 11/2012 | Berg |
| 2012/0316074 A1 | 12/2012 | Saxonov |
| 2012/0322058 A1 | 12/2012 | Regan et al. |
| 2013/0001083 A1 | 1/2013 | Quake et al. |
| 2013/0005599 A1 | 1/2013 | Klass et al. |
| 2013/0045882 A1 | 2/2013 | Klass et al. |
| 2013/0072389 A1 | 3/2013 | Penny et al. |
| 2013/0089855 A1 | 4/2013 | Mitsuhashi |
| 2013/0131194 A1 | 5/2013 | Skog et al. |
| 2013/0143314 A1 | 6/2013 | Shiels et al. |
| 2013/0149691 A1 | 6/2013 | Haj-Ahmad |
| 2013/0184169 A1 | 7/2013 | Klass et al. |
| 2013/0209528 A1 | 8/2013 | Levi et al. |
| 2013/0259924 A1 | 10/2013 | Bangel et al. |
| 2013/0273544 A1 | 10/2013 | Vlassov et al. |
| 2013/0287772 A1 | 10/2013 | Halbert et al. |
| 2013/0295574 A1 | 11/2013 | Skog et al. |
| 2013/0323831 A1 | 12/2013 | Han et al. |
| 2014/0004601 A1 | 1/2014 | Lim |
| 2014/0031256 A1 | 1/2014 | Lim |
| 2014/0050714 A1 | 2/2014 | Jensen et al. |
| 2014/0057310 A1 | 2/2014 | Fang et al. |
| 2014/0105964 A1 | 4/2014 | Bancel et al. |
| 2014/0105965 A1 | 4/2014 | Bancel et al. |
| 2014/0148502 A1 | 5/2014 | Bancel et al. |
| 2014/0155472 A1 | 6/2014 | Bancel et al. |
| 2014/0155473 A1 | 6/2014 | Bancel et al. |
| 2014/0155474 A1 | 6/2014 | Bancel et al. |
| 2014/0155475 A1 | 6/2014 | Bancel et al. |
| 2014/0161721 A1 | 6/2014 | Hatchwell et al. |
| 2014/0171400 A1 | 6/2014 | Goren et al. |
| 2014/0178888 A1 | 6/2014 | Vlassov et al. |
| 2014/0186432 A1 | 7/2014 | Bancel et al. |
| 2014/0193482 A1 | 7/2014 | Bancel et al. |
| 2014/0194319 A1 | 7/2014 | Skog et al. |
| 2014/0194494 A1 | 7/2014 | Bancel et al. |
| 2014/0194613 A1 | 7/2014 | Skog et al. |
| 2014/0199371 A1 | 7/2014 | Bancel et al. |
| 2014/0200262 A1 | 7/2014 | Bancel et al. |
| 2014/0200263 A1 | 7/2014 | Bancel et al. |
| 2014/0212871 A1 | 7/2014 | Comper et al. |
| 2014/0227766 A1 | 8/2014 | Gagnon |
| 2014/0234263 A1 | 8/2014 | Shiels |
| 2014/0255271 A1 | 9/2014 | Haj-Ahmad |
| 2014/0275229 A1 | 9/2014 | Bangel et al. |
| 2014/0287948 A1 | 9/2014 | Boniface et al. |
| 2014/0287950 A1 | 9/2014 | Hickok et al. |
| 2014/0309130 A1 | 10/2014 | Haj-Ahmad |
| 2014/0309292 A1 | 10/2014 | Jabado et al. |
| 2014/0326400 A1 | 11/2014 | Araci et al. |
| 2014/0329334 A1 | 11/2014 | Munoz |
| 2015/0004151 A1 | 1/2015 | Jensen et al. |
| 2015/0031616 A1 | 1/2015 | Conrad |
| 2015/0044695 A1 | 2/2015 | Lozupone et al. |
| 2015/0080410 A1 | 3/2015 | Hu et al. |
| 2015/0087536 A1 | 3/2015 | Brown et al. |
| 2015/0104793 A1 | 4/2015 | Quake et al. |
| 2015/0125950 A1 | 5/2015 | Lim et al. |
| 2015/0160230 A1 | 6/2015 | Taylor et al. |
| 2015/0182588 A1 | 7/2015 | Kahvejian et al. |
| 2015/0247190 A1 | 9/2015 | Ismagilov et al. |
| 2015/0306212 A1 | 10/2015 | Kahvejian et al. |
| 2015/0337356 A1 | 11/2015 | Baur et al. |
| 2015/0351389 A1 | 12/2015 | Kolari et al. |
| 2015/0361489 A1 | 12/2015 | Soper et al. |
| 2016/0004814 A1 | 1/2016 | Stamatoyannopoulos |
| 2016/0038557 A1 | 2/2016 | Pietrzkowski |
| 2016/0047735 A1 | 2/2016 | Grisham et al. |

OTHER PUBLICATIONS

Andrew F. Hill et al: "ISEV position paper: extracellular vesicle RNA analysis and bioinformatics", Journal of Extracellular Vesicles, (56) References Cited

OTHER PUBLICATIONS vol. 2, No. 1, Jan. 1, 2013 (Jan. 1, 2013), p. 22859, XP055638034, DOI: 10.3402/iev.v2i0.22859.
Jae-Hoon Lee et al: "Relationship Between 18F-Fluorodeoxyglucose Uptake and V-Ki-Ras2 Kirsten Rat Sarcoma Viral Oncogene Homolog Mutation in Colorectal Cancer Patients: Variability Depending on C-Reactive Protein Level", Medicine,Jan. 1, 2016 (Jan. 1, 2016), pp. e2236-e2236, XP055638511, United States DOI: 10.1097/MD. 0000000000002236 Retrieved from the Internet: URL: https://www.ncbi.nlm.nih.gov/pmc/artic les/PMC4706250/pdf/medi-95-e2236.pdf.
Fuxi Zhao et al: "Quantification and application of the placental epigenetic signature of the RASSFIA gene in maternal plasma", Prenatal Diagnosis, vol. 30, No. 8, Aug. 1, 2010 (Aug. 1, 2010), pp. 778-782, XP055255734, GB ISSN: 0197-3851, DOI: 10.1002/pd.2546.
Ping Yi et al: "Elevated Plasma Levels of Hypermethylated RASSFIA Gene Sequences in Pregnant Women with Intrahepatic Cholestasis", Cell Biochemistry and Biophysics, vol. 67, No. 3, Dec. 12, 2013 (Dec. 12, 2013), pp. 977-981, XP055208241, ISSN: 1085-9195, DOI:10.1007/s12013-013-9592-x.
Laigaard J et al: "ADAM12: a Novel First-Trimester Maternal Serum Marker for Down Syndrome", Prenatal Diagnosis, Chichester, Sussex, GB, vol. 23, No. 13, Dec. 30, 2003 (Dec. 30, 2003), pp. 1086-1091, XP008044595, ISSN: 0197-3851, DOI: 10.1002/PD.762.
Y M Dennis Lo et al: "Plasma placental RNA allelic ratio permits noninvasive prenatal chromosomal aneuploidy detection", Nature Medicine, vol. 13, No. 2, Jan. 7, 2007 (Jan. 7, 2007), pp. 218-223, XP055053181, ISSN 1078-8956, DOI: 10.1038/nm1530.
Hillary E Mulvey et al: "Extracellular vesicle-mediated phenotype switching in malignant and non-malignant colon cells", BMC Cancer, Biomed Central, London, GB, vol. 15, No. 1, Aug. 1, 2015 (Aug. 1, 2015), p. 571, XP021225634, ISSN: 1471-2407, DOI: 10.1186/S12885-015-1568-3.
Jennie Laigaard et al: "Maternal serum ADAM12 levels in Down and Edwards' syndrome pregnancies at 9-12 weeks' gestation", Prenatal Diagnosis, vol. 26, No. 8, Jan. 1, 2006 (Jan. 1, 2006), pp. 689-691, XP055638506, GBISSN: 0197-3851, DOI: 10.1002/pd.1480.
Chris Gardiner et al: "Techniques used for the isolation and characterization of extracellular vesicles: results of a worldwide survey", Journal of Extracellular Vesicles, vol. 5, No. 1, Jan. 1, 2016 (Jan. 1, 2016), p. 32945, XP055638040, DOI: 10.3402/jev.v5.32945.
Supplementary European Search Report for related application EP 17763841.8 dated Nov. 14, 2019, 5 pages.
AniteiM, WassmerT, StangeC, HoflackB. Bidirectional transport between the trans Golgi network and the endosomal system. Mol Membr Biol 2010;27:443-456.
Dean WL, Lee MJ, Cummins TD, Schultz DJ, Powell DW. Proteomic and functional characterisation of platelet microparticle size classes. Thromb Haemost 2009; 102: 711-718. 18.
Gercel-Taylor C, O'Connor SM, Lam GK, Taylor DD. Shed membrane fragment modulation of cd3-zeta during pregnancy: link with induction of apoptosis. J Repord Immunol 2002; 56:29-44.
György B, SzabóTG, PsztóiM,Pa'l Z, Misják P, Aradi B et al. Membrane vesicles, current state-of-the-art: emerging role of extracellular vesicles. Cell Mol Life Sci 2011;68:2667-2688.
H. Christina Fan, Noninvasive dianosis of fetal aneuploidy by shotgun sequencing DNA from maternal blood, Proceedings of the National Academy of Sciences of the United States of America, Jul. 13, 2008, pp. 1-6.
Hedlund M, Stenqvist A-C, Nagaeva O, et al. Human placenta express and secretes NKG2D ligands via exosomes that downmodulate the cognate receptor expression: evidence for immunosuppressive function. J Immunol. 2009; 183:340-351.
Holme PA, Orvim U, Hamers MJ, Solum NO, Brosstad FR, Barstad RM et al. Shearinduced platelet activation and platelet microparticle formation at blood flow conditions as in arteries with a severe stenosis. Arterioscler Thromb Vasc Biol 1997; 17: 646-653.
Hunter MP, Ismail N, Zhang X, Aguda BD, Lee EJ, Yu L et al. Detection of microRNA expression in human peripheralblood microvesicles. PLoS One 2008;3:e3694.
ISR/WO issued May 25, 2017 for application PCT/US2017/020987, 12 pages.
Kotsopouloua, Ioanna, et al. Non-invasive prenatal testing (NIPT): limitations on the way to become diagnosis. Diagnosis 2015; 2(3): 141-158.
Lucia Mincheva-Nilsson and Vladimir Baranov (2012). Placenta-Derived Exosomes and Their Role in the Immune Protection of the Fetus, Recent Advances in Research on the Human Placenta, Dr. Jing Zheng (Ed.), ISBN: 378-953-51-0194-9, InTech.
Ng EKO, Tsui NBY, Lam NYL, Chiu RWK, Yu SCH et al. presence of filterable and nonfilterable mRNA in the plasma of cancer patients and healthy individuals. Clin Chem 2002; 48:1212-1217.
Orlando KA, Stone NL, Pittman RN. Rho kinase regulates fragmentation and phagocytosis of apoptotic cells. Exp Cell Res 2006;312:5-15.
Ostrowski M, Carmo NB, Krumeich S, Fanget I, Raposo G, SavinaA et al. Rab27a and Rab27b control different steps of the exosome secretion pathway.NatCell Biol 2010; 12:19-30 Sup. pp. 1-13.
Peng P, Yan Y, Keng S. Exosomes in the ascites of ovarian cancer patients: Origin and effects on anti-tumor immunity. Oncol Rep 2011; 25:749-762.
Raposo G, Nijman HW, Stoorvogel W, Liejendekker R, Harding CV, Melief CJ et al. B lymphocytes secrete antigen-presenting vesicles. J Exp Med 1996;183:1161-1172.
Record M, Exosomal lipids in cell-cell communication. In Emerging concepts of Tumor Exosome-mediated cell-cell communication; Zhang H-G, Ed.; springer: New York, NY, USA, 2013; pp. 47-68.
Redman CWG, Sargent IL. Microparticles and immunomodulation in pregnancy and pre-eclampsia. J Reprod. Immunol. 2007; 76:61-67.
Sabapatha A, Gercel-Taylor C, Taylor DD. Specific isolation of placenta-derived exosomes from the circulation of pregnant women and their immunoregulatory consequences. A J Repord Immunol 2006; 56:345-355.
Taylor DD, Akyol S, Gercel-Taylor C. Pregnancy associated exosomes and their modulation of T cell signaling. J Immunol. 2006; 176:1534-1542.
Valadi H, Ekström K, Bossios A, Sjöstrand M, Lee JJ, Lötvall JO. Exosome-mediated transfer of mRNAs and microRNAs is a novel mechanism of genetic exchange between cells. NatCell Biol 2007;9:654-659.
Wolf P. The nature and significance of platelet products in human plasma. Br J Haematol 1967;13:269-288.
Decision to Grant a Patent in JP2018547407, dated Feb. 1, 2022, 3 pages.

NONINVASIVE MOLECULAR CONTROLS

REFERENCE TO RELATED APPLICATIONS

This application is national stage entry under 35 U.S.C. § 371(f) of PCT/US17/20987 entitled "NONINVASIVE MOLECULAR CONTROLS" filed Mar. 6, 2017, which claims the benefit of priority to U.S. Provisional Patent Application No. 62/304,712, filed Mar. 7, 2016, entitled "NONINVASIVE MOLECULAR CONTROLS", which are both incorporated by reference in their entirety.

BACKGROUND

Early detection of particular conditions or diseases in humans is desired. For example, early detection of pregnancy, a chromosomal abnormality of a fetus, or cancer may lead to a better prognosis for the patient as intervention-type therapies may be used. However, the available early detection mechanisms that yield a diagnosis, and not merely a screening for a condition or disease, typically require an invasive procedure (e.g. amniocentesis, colonoscopy, etc.). Invasive procedures have an increased risk of adverse reactions such as infection, infection transmission, reaction to anesthesia administered during the procedure, etc. Additionally, these invasive procedures are expensive and highly technical, and as such are not adapted for widespread use. Due to the increased risks and complications with these invasive procedures, it is desirable to have a noninvasive diagnostic test (e.g. a sample collected through a blood draw or urine) to test for a condition of interest.

Conventional noninvasive early detection mechanisms are valid as a screening for a condition of interest, but are not typically recommended as a diagnostic test. Additional detail regarding such conventional noninvasive early detection mechanisms may be found in Noninvasive diagnosis of fetal aneuploidy by shotgun sequencing DNA from maternal blood (Fan, H C, Blumenfeld, Y J, Chitkara, U, Hudgins, L, and Quake, S R. Proc Natl Acad Sci USA. 2008 Oct. 21; 105(42): 16266-16271) and Non-invasive prenatal testing (NIPT): limitations on the way to become diagnosis (Kotsopoulou, I, Tsoplou P, Mavrommatis, K, and Kroupis, C. Diagnosis 2015; 2 (3): 141-158.) The recommendation for use of such conventional noninvasive early detection mechanism as a screening test with follow-up invasive procedures to confirm diagnosis, often is due to the lack of appropriate internal quality controls when using the screening test to analyze a sample against in the noninvasive early detection mechanism.

To create a diagnostic test (e.g. a test that produces a diagnosis of a particular condition or disease), a sample (e.g. blood or urine) from a patient should be analyzed against a control to determine the presence or absence of a particular condition or disease. The control would preferably be a positive control, thus the control would have substantially the same composition as a sample with the condition of interest present. Further, the positive control may indicate that the diagnostic test methods produce analysis of the condition of interest (e.g. the analysis methods effectively isolate and analyze, either quantitatively or qualitatively, indicators of the condition of interest.) Such a diagnostic test could reduce or eliminate the need for costly and invasive diagnostic tests to determine the presence or absence of a condition of interest (particular condition or disease). As such, it also would be desirable to have a positive control allowing for a noninvasive diagnostic test of a sample to determine the presence or absence of a condition of interest in a sample.

SUMMARY

Noninvasive molecular controls and methods of using noninvasive molecular controls are described. In one aspect of the invention A method of making a noninvasive molecular control for determining the presence or absence of a condition of interest, the method comprising, predetermining a positive control for the condition of interest; selecting a first cell line for the positive control that produces a first extracellular vesicle with a first control marker for the condition of interest; amplifying the production of the first extracellular vesicle from the selected first cell line; isolating the produced control marker from the selected first cell line; quantifying the first control marker from the isolated first control marker; determining a volume of the first control marker for addition to an isolated control plasma; isolating the control plasma from a control sample; treating the isolated control plasma with a control stabilizer; determining a volume of the control plasma to add to the volume of the first control marker; combining the volume of the control plasma with the volume of the first control marker; and producing the noninvasive molecular control.

In another aspect of the invention, a method of analyzing a sample against a noninvasive molecular control to determine the presence or absence of a condition of interest, the method comprising: quantifying a first control marker in the sample; quantifying the first control marker in the noninvasive molecular control; determining the presence or absence of the condition of interest, the determining comprising comparing an indicated percentage of the first control marker in the noninvasive molecular control to a predetermined threshold of the first control marker in the sample, wherein the predetermining of the noninvasive molecular control comprises, predetermining a positive control for the condition of interest; pre-selecting a first cell line for the positive control where the preselected first cell line produces a first extracellular vesicle with the first control marker for the condition of interest; amplifying the production of the first extracellular vesicle from the selected first cell line; isolating the produced first control marker from the selected first cell line; quantifying the first control marker from the isolated first control marker; determining a volume of the first control marker for addition to an isolated control plasma; isolating the control plasma from a control sample; treating the isolated control plasma with a control stabilizer; determining a volume of the control plasma to add to the volume of the first control marker; and combining the volume of the control plasma with the volume of the control marker to produce the noninvasive molecular control.

In another aspect of the invention, a method of analyzing a sample against a noninvasive molecular control to determine the presence or absence of a condition of interest, the method comprising: quantifying a secondary control marker in the sample; quantifying the secondary control marker in the noninvasive molecular control; determining the presence or absence of the condition of interest, the determining comprising comparing an indicated percentage of the secondary control marker in the noninvasive molecular control to a predetermined threshold of the control marker in the sample, wherein the predetermining of the noninvasive molecular control comprises, predetermining a positive control for the condition of interest; pre-selecting a first cell line for the positive control that produces extracellular vesicles with a first control marker for the condition of interest; amplifying the production of extracellular vesicles from the selected first cell line; isolating the produced control marker from the selected first cell line; quantifying the first control marker from the isolated control marker; determining a volume of the first control marker for addition to an isolated control plasma; isolating the control plasma from a control sample; treating the isolated control plasma with a control stabilizer; determining a volume of the control plasma to add to the volume of the first control marker; combining the volume of the control plasma with the volume of the first control marker; pre-selecting a second cell for the positive control that produces a second extracellular vesicles with a secondary control marker for the condition of interest amplifying the production of the second extracellular vesicle from the selected second cell line; isolating the produced second control marker from the selected second cell line; quantifying the second control marker from the isolated second control marker; determining a volume of the second control marker for addition to the isolated control plasma; combining the volume of the secondary control marker with the volume of the control plasma and the volume of the first control marker; and producing the noninvasive molecular control.

In another aspect of the the invention, a noninvasive molecular control comprising, a first control marker comprising from 10 to 20 percent of the total volume of the noninvasive molecular control, wherein the first control marker is selected from a group consisting of hypermethylated ras association domain-containing protein promoter region, centromere of chromosome 21, and kirston rat sarcoma viral oncogene homolog exon 2 G13D; a control filler from 10 to 30 percent (weight/volume) of the total volume of the noninvasive molecular control, wherein the control filler is selected from a group consisting of hypomethylated ras association domain-containing protein promoter region and wild type kirston rat sarcoma viral oncogene homolog exon 2 G13D; a control stabilizer comprising from 0.1 to 5 percent (weight/volume) of the total volume of the noninvasive molecular control; and a control plasma comprising from 30 to 80 percent (weight/volume) of the total volume of the noninvasive molecular control, wherein the control plasma is a biological fluid.

In another aspect of the invention, a noninvasive molecular control comprising, a first control marker comprising from 250 to 750 copies of the control markers per milliliter, wherein the first control marker is placenta-specific 4 messenger ribonucleic acid; a control plasma comprising from 30 to 80 percent (weight/volume) of the total volume of the noninvasive molecular control, wherein the control plasma is a biological fluid; and a control stabilizer selected from the group consisting of 2-bromo-2nitropropane-1 from 0.05-0.5% weight/volume, 3-diol, aminocaproic acid from 0.1%-0.5% weight/volume, imidazolidinyl urea from 0.15%-0.2% weight/volume, and combinations thereof.

In another aspect of the invention, a noninvasive molecular control comprising, a first control marker comprising from 0.15 to 0.5 micrograms per milliliter, wherein the first control marker is metalloprotease protein 12; a control plasma comprising from 30 to 80 percent (weight/volume) of the total volume of the noninvasive molecular control, wherein the control plasma is a biological fluid; and a control stabilizer selected from the group consisting of 2-bromo-2nitropropane-1 from 0.05-0.5% weight/volume, 3-diol, aminocaproic acid from 0.1%-0.5% weight/volume, imidazolidinyl urea from 0.15%-0.2% weight/volume, and combinations thereof.

The following detailed description is exemplary and explanatory only and is not necessarily restrictive of the invention as claimed. The accompanying drawings, which are incorporated in and constitute a part of the specification, illustrate embodiments of the invention and together with the detailed description, serve to explain the principles of the invention.

BRIEF DESCRIPTION OF THE DRAWINGS

The numerous advantages of the present invention may be better understood by those skilled in the art by reference to the accompanying FIGURES in which.

DETAILED DESCRIPTION

A method of making noninvasive molecular controls and analysis using the noninvasive molecular controls is described. The method of making the noninvasive molecular controls includes, predetermining a positive control for a condition of interest, selecting a cell line with a control marker for the condition of interest, amplifying production of extracellular vesicles containing the control marker from the selected cell line, isolating the produced control marker from the selected cell line, quantifying the control marker from the isolated extracellular vesicles, determining a volume of the control marker for addition to an isolated control plasma, isolating the control plasma from a control sample, treating the isolated control plasma with a control stabilizer, determining a volume of the control plasma to add to the volume of control marker, combining the volume of the control marker with the isolated control plasma, and analyzing a sample against the noninvasive molecular control. The resulting noninvasive molecular control includes a control marker, a control stabilizer, and a control plasma. The noninvasive molecular control may further include a control filler. The noninvasive molecular control is a positive control used to analyze a sample to test for the presence or absence of a condition of interest. The preferred noninvasive molecular control is a positive control that contains the control marker of the condition of interest in proportions substantially similar to a human being having the condition of interest. Such positive control may then be used to measure a sample against, and thus to detect the presence or absence of the condition of interest.

A condition of interest is a condition or disease where early detection is desired. For example, the condition of interest may be a human pregnancy, a chromosomal abnormality of a human fetus (e.g. trisomy 21, trisomy 18), or a human cancer (e.g. colon cancer). Each condition of interest produces a control marker in the human being that is unique to the condition of interest.

Control markers are found on cfDNA, mRNA, and proteins in an extracellular vesicle (e.g. microvesicles and exosomes). Extracellular vesicles are produced by a cell, and contain biomarkers (e.g. membrane receptors, adhesion molecules, cytokines, chemokines, growth factors, mRNAs and miRNAs, cfDNA, etc.), which reflect the cellular origin and the physiological state of the cell from which it came. In the present method, the control marker found in extracellular vesicles may be cfDNA (e.g. dsDNA found in an extracellular vesicle). In the present method, the control marker may be mRNA in extracellular vesicles. Further, in the present method, the control marker may be a protein (e.g. membrane receptor, cytokine, adhesion molecule, and the like) in extracellular vesicles. The control marker may be a mutated gene, a chromosomal abnormality, an mRNA abnormality, or a protein abnormality. Because the control marker is found on the cfDNA, mRNA, and protein of extracellular vesicles, a noninvasive test (e.g. blood draw or urine sample) may be used to detect the presence or absence of the condition of interest in a sample.

A sample used to determine the presence or absence of the condition of interest may be blood from a human. When the sample is human blood it may be collected via a blood draw and subjected to a two stage centrifugation protocol to obtain plasma that is substantially free of cells and cellular debris. The human blood sample may be centrifuged at 1600 $(1.118 \times 10^{-5})$ (e.g. xg) for 10 minutes at room temperature. The plasma portion of the blood sample may then be transferred without disruption of the buffy coat to a new centrifugation tube and subject to centrifugation at 16,000 g for 10 minutes at room temperature to separate remaining cells and cellular debris from the plasma. The resulting plasma from the human blood sample is substantially free of cells and cellular debris, and contains extracellular vesicles. The biomarker (control marker) identifying the presence or absence of the condition of interest is then isolated from the extracellular vesicles in the plasma. When the biomarker is cfDNA it may be isolated via a commercial kit that may utilize a column elution protocol with a silica-based membrane for binding, such as QIAGEN circulating nucleic acid isolation kit. When the biomarker is mRNA it may be isolated via a commercial kit that may utilize a column elution protocol with a cellulose-based membrane for binding. When the biomarker is protein the isolation may include homogenization, such as via sonication for one minute, where the sonication may occur on ice. The resulting homogenate includes the protein biomarker. When the sample is human urine it may be collected via a clean urine catch protocol. The urine sample may then be subjected to centrifugation at 2000 g for 30 minutes at room temperature. The resulting supernatant is substantially free of cells and cellular debris and contains extracellular vesicles. When the biomarker is cfDNA it may then be isolated from the extracellular vesicles in the urine supernatant via a commercial kit that may utilize a column elution protocol with a silica-based membrane for binding, such as QIAGEN circulating nucleic acid isolation kit. When the biomarker is mRNA it may be isolated via a commercial kit that may utilize a column elution protocol with a cellulose-based membrane for binding. When the biomarker is a protein it may be isolated via disrupting extracellular vesicles. When the biomarker is protein the isolation may include homogenization, such as via sonication for one minute, where the sonication may occur on ice. The resulting homogenate includes the protein biomarker.

Figure 1:
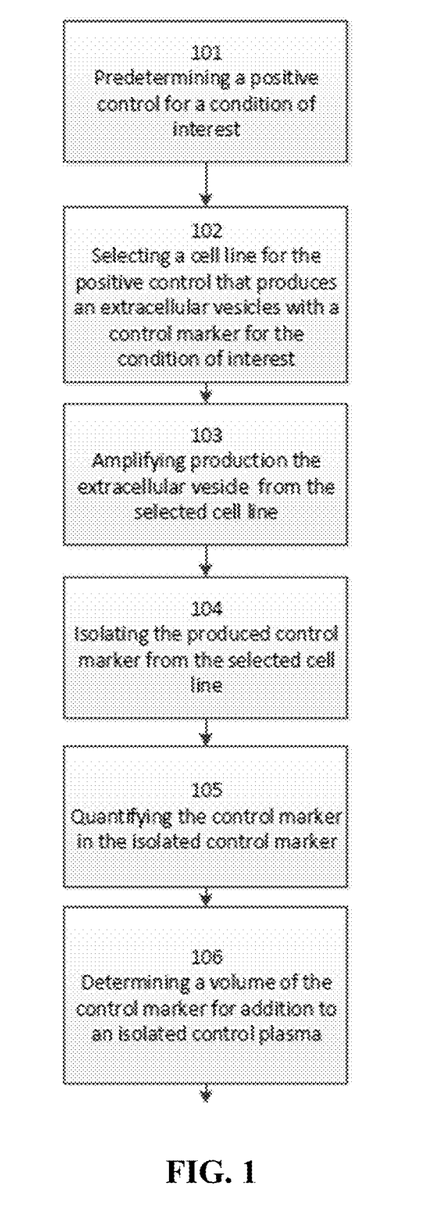
FIG. 1 illustrates a method for making a noninvasive molecular control.

A method 100 is used to make a noninvasive molecular control. The noninvasive molecular control includes a control marker, a control stabilizer, and a control plasma. The noninvasive molecular control may include a control filler.

In 101 a positive control for a condition of interest is predetermined. The condition of interest is a disease or condition where early detection is desired, such as human pregnancy, Trisomy 21, Trisomy 18, or human colon cancer. The control marker for the positive control is selected based upon the expression of a biomarker in the sample unique to the condition of interest. The biomarker may be cfDNA, found in extracellular vesicles (e.g. dsDNA found in extracellular vesicles), that is mutated or contains a chromosomal abnormality. The biomarker may be mRNA, found in extracellular vesicles, that is specific for a certain disease or condition (abnormal). Further, the biomarker may be a protein, found in extracellular vesicles, that is specific for a disease or a condition (abnormal). The biomarker determines the selection of the control marker, as the control marker is substantially similar to the biomarker (e.g. the biomarker and the control marker are the same mutated gene, mutation, chromosomal abnormality, chromosome aneuploidy, disease specific mRNA, disease specific microRNA or disease specific proteins). The noninvasive molecular control is a positive control that contains the control marker of the condition of interest. The positive control may contain the control marker in proportions substantially similar to the biomarker in the sample with the condition of interest.

In 102 a cell line that produces the predetermined control marker is selected for the positive control. The cell line may be primary cultured cells (e.g. cells isolated and cultured from a biologic tissue, such as a tumor) or another human cell line (e.g. established cell lines) that produces the control marker specific to the biomarker of the condition of interest. The control marker may be a genetically altered gene, such as mutated DRAS, p53, BRCA 1, BRCA 2. The control marker may be a genetically altered (mutated) mRNA. The control marker may be normal mRNA in abnormal quantities. The control marker may be a protein having an abnormality (e.g. structural deficiency, abnormal amount, or the like). The cell line produces extracellular vesicles containing cfDNA, mRNA, microRNA or protein with the control marker. Therefore, the cell line is selected dependent on the cfDNA, mRNA, microRNA or protein released from the cell line, which contains the control marker.

For example, when human pregnancy is the condition of interest, the control marker may be the ras association domain-containing protein 1 (e.g. RASSF1A) promoter region that is hypermethylated (e.g. hypermethylated RASSF1A). In a pregnant female human (e.g. the mother), the biomarker is fetal cfDNA that contains hypermethylated RASSF1A that is present in extracellular vesicles of the mother. The mother also has cfDNA produced from her own cells with a hypomethylated RASSF1A promoter region (e.g. hypomethylated RASSF1A). A non-pregnant female human does not have fetal cfDNA with hypermethylated RASSF1A, only cfDNA with hypomethylated RASSF1A. Therefore, the cell line when the condition of interest is pregnancy is the TOV 21G cell line, which produces extracellular vesicles containing cfDNA with hypermethylated RASFF1A. The TOV 21G cell line is a human cell line isolated and cultured from a human female ovarian epithelial cell with grade 3, stage III, primary malignant adenocarcinoma, clear cell carcinoma.

Additionally, when human pregnancy is the condition of interest, the control marker may be placenta-specific 4 (PLAC4) mRNA. In the mother, the biomarker is fetal PLAC4 mRNA present in extracellular vesicles of the mother. A non-pregnant female human does not have fetal extracellular vesicles containing PLAC4 mRNA. Therefore, the cell line when the condition of interest is pregnancy may be the JAR cell line, which produce extracellular vesicles containing PLAC4 mRNA. The JAR cell line is a human cell line isolated and cultured from a human female placenta where the fetus had choriocarcinoma.

Further, when human pregnancy is the condition of interest, the control marker may be metalloprotease protein 12 (ADAM12) placental protein. In the mother, the biomarker is ADAM12 placental protein in extracellular vesicles of the mother. A non-pregnant female human does not have fetal extracellular vesicles containing ADAM12 placental protein. Therefore, the cell line when the condition of interest is pregnancy may be the JAR cell line, which produces extracellular vesicles containing ADAM12 placental protein.

When Triosomy 21 in a human fetus (e.g. fetus) is the condition of interest the control marker may be the centromere of chromosome 21. Fetal cfDNA of a fetus with Trisomy 21 contains three copies of chromosome 21, and therefore three copies of the centromere of chromosome 21. In a mother with a fetus having Trisomy 21, the biomarker is fetal cfDNA that contains three copies of the centromere of chromosome 21, which are present in extracellular vesicles of the mother. The mother also has cfDNA produced from her own cells with two copies of the centromere of chromosome 21. Therefore, the cell line when the condition of interest is Trisomy 21 may be Detroit 532, which produces cfDNA with three copies of the centromere of chromosome 21. The Detroit 532 cell line is a human cell line isolated and cultured from a human male fibroblast cell.

Further, when Trisomy 21 in the fetus is the condition of interest the control marker may be fetal PLCA4 mRNA. Fetal mRNA of a fetus with Trisomy 21 contains three copies of chromosome 21, and therefore additional expression of mRNA transcribed from the DNA of all three copies of chromosome 21. Therefore, the fetus having Trisomy 21 will have an expression of fetal PLAC4 that is higher than that of a fetus without Trisomy 21. As such, the cell line when the condition of interest is Trisomy 21, may be the JAR cell line, which produces PLAC4 mRNA.

When Trisomy 18 in the fetus is the condition of interest the control marker may be ADAM12 placental protein. Expression of ADAM12 placental protein is suppressed in a fetus with Trisomy 18. Therefore, the fetus having Trisomy 18 will have an expression of ADAM12 placental protein that is lower than that of a fetus without Trisomy 18. As such, the cell line when the condition of interest is Trisomy 18, may be the JAR cell line, which produces ADAM12 placental protein.

When human colon cancer is the condition of interest the control marker is kirston rat sarcoma viral oncogene homolog (KRAS) exon 2 G13D with a heterozygous mutation. A human with colon cancer produces the biomarker of cfDNA with a heterozygous mutation of KRAS exon 2 G13D. Therefore, the cell line when the condition of interest is human colon cancer is HCT116 as it produces cfDNA with a heterozygous mutation of KRAS exon 2G13D. The HCT 116 cell line is a human cell line isolated and cultured from a male epithelial colon cell with colorectal carcinoma.

In 103, the release of the control marker from the cell line is amplified. The cell lines may be induced by chemicals and other treatments to amplify the production of extracellular vesicles, which contain the control marker in the extracellular vesicles when the cell line is still in a culture medium. These chemicals and other treatments include, subjecting cell lines to hypoxia or glucose deprivation, or adding chemical compounds, such as hypoxia-inducible factor (HIF) hydroxylase inhibitor dimethyloxaloylglycine (DMOG), a 2-oxoglutarate analogue at an approximately 1 to 3 millimolar (mM) concentration, adenosine triphosphate (ATP) at an approximately 1 to 5 mM concentration, or ionophore (2S,3R,4S)-4-[(2S,5R,7S,8R,9S)-2-[(2R,5S)-5-ethyl-5-[(2R,3 S,5R)-5-[(2S,3 S,5R,6R)-6-hydroxy-6-(hydroxymethyl)-3,5-dimethyloxan-2-yl]-3-methyloxolan-2-yl]oxolan-2-yl]-7-hydroxy-2,8-dimethyl-1,10-dioxaspiro[4.5]decan-9-yl]-3-methoxy-2-methylpentanoic acid (monensin) at an approximately 1 to 10 micromolar (µM) concentration.

For example, when the cell line is TOV 21G, the cell line is treated with ionophore monensin at an effective concentration from 5-15 µM, under conditions of 37 degrees Celsius in a humidified atmosphere of 5% carbon dioxide for at least 1 day. When the cell line is Detroit 532 the cell line is treated with ionophore monensin at an effective concentration from 5-15 µM under conditions of 37 degrees Celsius in a humidified atmosphere of 5% carbon dioxide for at least 1 day.

When the cell line is JAR cells and the control maker is PLAC4 mRNA, the cell line is treated with ionophore Monesin at an effective concentration from 5-15 µM under conditions of 37 degrees Celsius in a humidified atmosphere of 5% carbon dioxide for at least 1 day. When the cell line is JAR cells and the control marker is ADAM12 placental protein, the cell line is treated with with ionophore Monesin at an effective concentration from 5-15 µM under conditions of 37 degrees Celsius in a humidified atmosphere of 5% carbon dioxide for at least 1 day. When the cell line is HCT 116 the cell line is treated with ionophore monensin at an effective concentration from 5-15 µM under conditions of 37 degrees Celsius in a humidified atmosphere of 5% carbon dioxide for at least 1 day. As used herein effective concentration means the concentration of ionophore monensin in solution taking into account the chemical potential of ionophore monensin in real solution.

In 104, the control marker in extracellular vesicles is isolated from a cell culture medium of the cell lines. The cell lines release the extracellular vesicles containing the cfDNA into the cell culture medium. The extracellular vesicles may be isolated from the cell culture medium using an exosome isolation kit for total exosome isolation from cell culture media. For example, total exosome isolation kits may contain sodium azide to act as the chemical that isolates the extracellular vesicles (e.g. total exosome isolation reagent). A protocol using the total exosome isolation kit is followed to isolate the extracellular vesicles. For example, collection and centrifugation of the cell culture media at 2000×(1.118×$10^{-5}$) (e.g. ×g) for 30 minutes at room temperature is done to remove cells and other cellular and biological debris. After centrifugation the cell culture media containing the extracellular vesicles is transferred to a collection tube (e.g. test tube) and is mixed with a volume (e.g. 25 mL) of the total exosome isolation reagent. The cell culture media is then incubated at 4 degrees overnight (e.g. approximately 12 hours). After overnight incubation the cell culture media is centrifuged at 10,000×g for 1 hour at 4 degrees Celsius. After centrifugation the supernatant contains the remaining cellular and biological debris and is aspirated and discarded. The extracellular vesicles remain in an extracellular vesicle pellet, which may be further suspended in phosphate-buffered saline (PBS) and stored at minus 80 degrees Celsius. The control marker is then isolated from the extracellular vesicles in the extracellular vesicle pellet. When the control marker is cfDNA it may be isolated via a commercial kit that may utilize a column elution protocol with a silica-based membrane for binding, such as QIAGEN circulating nucleic acid isolation kit. When the control marker is mRNA it may be isolated via a commercial kit that may utilize column elution protocol with a cellulose-based membrane for binding. When the control marker is protein the isolation further includes sonication of the extracellular vesicle pellet, such as sonication for approximately one minute on ice.

In 105, the control marker is quantified from the isolated control marker. When the control marker is cfDNA, the number of control marker copies are quantified using droplet digital polymerase chain reaction (ddPCR). When the control marker is mRNA, the number of control marker copies are quantified using reverse transcription ddPCR. When the control marker is protein, the number of control marker copies are quantified using enzyme linked immunosorbent assay (ELISA). The quantification may then be converted to give a concentration of control marker, such as copies per volume (e.g. copies/mL), or microgram per volume (micrograms/mL).

In 106, a volume of the control marker is determined to add to an isolated control plasma. The volume makes up a corresponding percentage of the noninvasive molecular control. When the control marker is hypermethylated RASSF1A, the control marker may be 10%, 15%, or 20% of the total volume of the noninvasive molecular control (e.g. the control marker is 10% of the total volume of cfDNA in the noninvasive molecular control), as determined by the gestational age of the subject's fetus to be tested. In a pregnant human the percentage of fetal cfDNA with hypermethylated RASSF1A increases as the gestational age of the fetus increases, changing the composition of the total RASSF1A composition, with the percentages being approximately 10% during the first trimester, approximately 15% during the second trimester, and approximately 20% during the third trimester.

For example, if 100 milliliter (mL) of a first trimester noninvasive molecular control is desired, then the percentage of hypermethylated RASSF1A is preferably adjusted to approximately 10%. cfDNA concentration in the non-pregnant human ranges from approximately 1000-1500 copies/mL of plasma, which is also the same equivalent of the hypomethylated RASSF1A of 1000-1500 copies/mL. The number of RASSF1A (both hypomethylated and hypermethylated) copies in a pregnant human during pregnancy increases to approximately 1,800 per mL, if the upper end of the hypomethylated RASSF1A concentration is used from the non-pregnant human concentration. Therefore, the noninvasive molecular control for the first trimester preferably includes a concentration of 180 copies/mL of hypermethylated RASSF1A (i.e. the control marker), and a concentration of 1620 copies/mL of a control filler.

If the noninvasive molecular control is for the second trimester it preferably includes a concentration of 270 copies/mL of hypermethylated RASSF1A, and a concentration of 1530 copies/mL of a control filler. If the noninvasive molecular control is for the third trimester it preferably includes a concentration of 360 copies/mL of hypermethylated RASSF1A, and a concentration of 1440 copies/mL of a control filler. When the control marker is hypermethylated RASSF1A, the control filler is hypomethylated RASSF1A.

The volume of the control marker to be added is determined by the equation $Y=(A \times V)/X$, where Y is the volume of the control marker to be added to the noninvasive molecular control, A is the concentration of the control marker (e.g. copies/mL, micrograms/mL) needed in the noninvasive molecular control, V is the total volume of the noninvasive molecular control, and X is the concentration (e.g. copies/mL, micrograms/mL) of the isolated control marker. For a 100 mL first trimester molecular control, A is 180 copies/mL of hypermethylated RASSF1A, V is 100 mL, and X is 35,000 copies/mL. Y is (180 copies/mL×100 mL)/35,000 copies/mL, and Y equals 0.514 mL.

When the noninvasive molecular control includes a control filler, the volume of the control filler copies to be added is determined by the equation $R=((S-A) \times V)/Z$, where R is the volume (e.g. mL) of the control filler, in this example hypomethylated RASSF1A, to be added to the noninvasive molecular control, S is the desired concentration (e.g. copies/mL, micrograms/mL) of RASSF1A copies (hypomethylated+hypermethylated) in the noninvasive molecular control, A is the concentration (e.g. copies/mL) of the control marker in the control plasma, V is the total volume of the noninvasive molecular control, and Z is the concentration (e.g. copies/mL) of a hypomethylated RASSFA1A stock solution.

The hypomethylated RASSF1A stock solution may be obtained either through isolation of extracellular vesicles from primary human dermal fibroblast cells or isolation of extracellular vesicles from non-pregnant human female blood, utilizing the same protocol as in 104. The concentration of the hypomethylated RASSF1A stock solution is determined by extracting cfDNA from a predetermined volume of the hypomethylated RASSF1A stock solution and quantifying the RASSF1A copy number by ddPCR. For a 100 mL first trimester molecular control, S is 1800 copies/mL, A is 180 copies/mL, V is 100 mL, and Z is 150,000 copies/mL. R is (1800 copies/mL–180 copies/mL)×100 mL/150,000 copies/mL, and R equals 1.08 mL.

When the condition of interest is human pregnancy, the control marker may be PLAC4 mRNA, where the control marker may of a concentration of 250, 500, and 750 (copies/mL of the noninvasive molecular control), as determined by the gestational age of the subject's fetus to be tested. In a pregnant human the concentration of PLAC4 mRNA increases as the gestational age of the fetus increases, changing the composition of the PLAC4 mRNA in extracellular vesicles, with the concentrations being approximately 250, 500, and 750 copies/mL of the noninvasive molecular control during the first, second, and third trimesters, respectively. In a non-pregnant human female, PLAC4 mRNA in extracellular vesicles is not present, and therefore no control filler is in the noninvasive molecular control. The volume of control marker to be added is determined by the equation $Y=(A \times V)/X$.

When the condition of interest is human pregnancy, the control marker may be ADAM12 protein, where the control marker concentration may be from 0.15 to 0.50 (micrograms/mL of the noninvasive molecular control). Preferably, the control marker is 0.15 micrograms/mL. In a non-pregnant human female ADAM12 in extracellular vesicles is not present, and therefore no control filler is in the noninvasive molecular control. The volume of control marker to be added is determined by the equation $Y=(A \times V)/X$.

When the condition of interest is Trisomy 21, the control marker may be the centromere of chromosome 21, the control marker may be 10%, 15%, or 20% of the total volume of the noninvasive molecular control, as determined by the gestational age of the subject's fetus to be tested. When the condition of interest is Trisomy 21, there is also a secondary control marker of hypermethylated RASSF1A, which is the control to test for the presence or absence of fetal cfDNA. The secondary control marker may be 10%, 15%, or 20% of the total concentration in the noninvasive molecular control, as determined by the gestational age of the subject's fetus to be tested. When the condition of interest is Trisomy 21, the control filler is hypomethylated RASSF1A. In a pregnant human the percentage of fetal cfDNA with hypermethylated RASSF1A increases as the gestational age of the fetus increases, changing the composition of the total RASSF1A composition, with the percentages being approximately 10% during the first trimester, approximately 15% during the second trimester, and approximately 20% during the third trimester. The proportion of the control marker and the secondary control marker in the noninvasive molecular control is substantially similar to the percentage of fetal cfDNA in a pregnant human. The volume of the control marker to be added is determined by the equation $Y=(A \times V)/X$. The volume of the secondary control marker to be added is determined by the equation $Y=(A_2 \times V)/X$, where $A_2$ is the concentration of the secondary control marker (copies/mL) needed in the noninvasive molecular control. The volume of the control filler (e.g. hypomethylated RASSF1A) to be added is determined by the equation $R=((S-(A+A_2)) \times V)/Z$. For a 100 mL noninvasive molecular control for the first trimester when the condition of interest is Trisomy 21, S is 1800 copies/mL, A is 180 copies/mL, $A_2$ is 180 copies/mL V is 100 mL, and Z is 150,000 copies/mL, and R equals 0.96 mL.

When the condition of interest is Trisomy 21, the control marker may may be PLAC4 mRNA. The concentration of the control marker may be 250, 500, and 750 copies/mL of the noninvasive molecular control, as determined by the gestational age of the subject's fetus to be tested. In a non-pregnant human female PLAC4 mRNA is not present, and therefore no control filler or secondary control is in the noninvasive molecular control. The volume of the control marker to be added is determined by the equation $Y=(A \times V)/X$.

When the condition of interest is Trisomy 18, the control marker may be ADAM12 placental protein. The control marker may is from 0.15 to 0.50 (micrograms/mL) of the noninvasive molecular control. Preferably, the control marker is 0.15 micrograms/mL. In a pregnant human with a fetus having Trisomy 18, the concentration of ADAM12 is approximately 0.10 (micrograms/mL of plasma). In a non-pregnant human female ADAM12 in extracellular vesicles is not present, and therefore no control filler or secondary control marker is in the noninvasive molecular control. The volume of the control marker to be added is determined by the equation $Y=(A \times V)/X$. The concentration of the control marker in the noninvasive molecular control is substantially similar to the concentration of ADAM12 in a pregnant human with a normal fetus.

When the condition of interest is colon cancer, the control marker is KRAS exon 2 G13D with a heterozygous mutation, and the control filler is the wild type KRAS gene. The control filler (e.g. wild-type KRAS) may be obtained from blood of a human donor or from a cell line that produces the control filler. The cell line may be primary cultured cells (e.g. cells isolated and cultured from a biologic tissue, such as a tumor, skin tissue, or the like) or another human cell line (e.g. established cell lines) that produces the control filler, which may be isolated pursuant to the protocol in 104. The control marker may be 10%, 15%, or 20% of the total volume of the noninvasive molecular control. The total concentration of the control marker and the control filler is 1800 copies/mL. The volume of the control marker to be added is determined by the equation $Y=(A \times V)/X$. The volume of the control filler to be added is determined by the equation $R=((S-A) \times V)/Z$.

In 107, the control plasma is isolated from a control sample. The control plasma is a biological fluid, such as human blood, animal blood, artificial plasma, or synthetic urine. When the sample is human blood, the control plasma may be isolated from a control sample, or it may be an artificial plasma of artificial constituents. The artificial plasma may be the following combined artificial constituents in the stated amounts: human serum albumin of 80 grams (e.g. g), tri-potassium ethylenediaminetetraacetic acid ($K_3EDTA$) of 1.7 g, 2-bromo-2nitropropane-1, 3-diol of 1 g, Aminocaproic acid of 1 g, imidazolidinyl (IDU) of 2 g, bilirubin of 0.0001 g, sodium chloride (NaCl) of 8 g, potassium chloride (KCl) of 0.2 g, disodium phosphate ($Na_2HPO_4$) of 1.44 g, and monopotassium phosphate ($KH_2PO_4$) of 0.24 g dissolved in 800 mL of distilled water with a pH adjustment to 7.4 using hydrocholoride (HCl). The volume is then adjusted to 1 liter by adding distilled water. The artificial plasma may then be sterilized by autoclaving for approximately 20 minutes at about 15 pounds per square inch (lb/sq. in.) on a liquid cycle of an autoclave. The artificial plasma may then be stored at low temperature, such as −80° C., until use.

The control sample may be blood from any animal source, such as, human, bovine, porcine, horse, bird, or fish. When the control blood is human blood, the control plasma may be isolated by two state centrifugation. The control plasma is first separated from blood by centrifugation at about 1600×g at room temperature for 10 minutes. The control plasma is then removed without disturbance of the buffy coat and is transferred to a new centrifugation tube and centrifuged at 16,000×g for 10 minutes at room temperature. The control plasma, which is now clarified, is removed without substantially disturbing the centrifugation pellet. When the control blood is of a non-human source, the control plasma may be isolated by a two stage centrifugation protocol to remove endogenous extracellular vesicles. The control plasma is first separated from blood by centrifugation at 1600×g at room temperature for 10 minutes. The control plasma is then removed without disturbance of the buffy coat and is transferred to a new centrifugation tube and centrifuged at 100,000×g for 2 hours at 4° C. The control plasma, which is now clarified, is removed without substantially disturbing the centrifugation pellet. The control plasma may be stored at −80° C.

When the sample is human urine, the control plasma may be synthetic urine. The synthetic urine may be a combination of artificial constituents, such as sodium sulfate 2 grams (e.g. g), ammonium dihydrogenphosphate 0.85 g, ammonium hydrogenphosphate 0.15 g, calcium chloride dehydrate 0.25 g, magnesium chloride hexahydrate 0.5 g, potassium chloride 2 g, tri-potassium ethylenediaminetetraacetic acid (K3EDTA) of 1.7 g, 2-bromo-2nitropropane-1, 3-diol of 1 g, aminocaproic acid of 1 g, imidazolidinyl urea (IDU) of 2 g, bilirubin of 0.0001 g and urea 0.2 g dissolved in 800 mL of distilled water. The volume of the synthetic urine is then adjusted to 1 liter by adding distilled water. The synthetic urine may then be sterilized by autoclaving for 20 minutes at 15 pounds per square inch (lb/sq. in.) on a liquid cycle of an autoclave. The synthetic urine may then be stored at −80° C. until use.

In 108, the control plasma is treated with a control stabilizer to inhibit protease activity. The control stabilizer may be 2-bromo-2nitropropane-1, 3-diol in a concentration from 0.05-0.5% weight/volume, with preferred concentration of 0.1% weight/volume, where concentrations less than 0.05% weight/volume and greater than 0.5% weight/volume are not effective for stabilization of the control plasma. The control stabilizer may be aminocaproic acid in a concentration from 0.1%-0.5% weight/volume, with preferred concentration of 0.1% weight/volume, where concentrations less than 0.1% weight/volume and greater than 0.5% weight/volume are not effective for stabilization of the control plasma. The control stabilizers may further include imidazolidinyl urea in a concentration from 0.15%-0.2% weight/volume, with the preferred concentration at 0.2% weight/volume, where concentrations less than 0.15% weight/volume and greater than 0.2% weight/volume are not effective to stabilize extracellular vesicle membranes.

In 109, a volume of the control plasma is determined to add to the volume of the control marker and control stabilizer. For example, if the desired volume of the noninvasive molecular control is 100 mL, the desired percentage of the control marker is determined in 107, and the volume of control plasma with the control stabilizer to be added is determined by the equation C=V−R, where C is the volume of the control plasma to be added, V is the total volume of the noninvasive molecular control, Y is the volume of control marker to be added. When the noninvasive molecular control includes a control filler, the volume of the control plasma is determined by the equation C=V−(Y+R) where R is the volume of the control filler.

In 110, the volume of the control marker with control stabilizer is combined to the volume of the control plasma, such as in a collection tube to produce the noninvasive molecular control.

In 111, a sample is analyzed against the noninvasive molecular control to determine the presence or absence of the condition of interest. The biomarker is extracted from the sample and the noninvasive molecular control simultaneously. When the biomarker is cfDNA the extraction is via a commercial kit that may utilize a column elution protocol with a silica-based membrane for binding, such as QIAGEN circulating nucleic acid isolation kit. The cfDNA from the sample and the noninvasive molecular control is quantified and the quantification values are compared to determine that requisite levels of cfDNA are present to further analyze. The cfDNA from the sample and the noninvasive molecular control is then sequenced, via a DNA sequencing method, such as massively parallel DNA sequencing, to determine the presence or absence of the control marker indicating the presence or absence of the condition of interest.

When the biomarker is mRNA the extraction is via a commercial kit that may utilize a column elution protocol with a cellulose-based membrane for binding. The mRNA from the sample and the noninvasive molecular control is quantified and the quantification values are compared to determine that requisite levels of mRNA are present to further analyze. The mRNA from the sample and noninvasive molecular control is then sequenced, via an mRNA sequencing method, such as reverse transcriptase ddPCR or reverse transcriptase real time PCT, to determine the presence or absence of the control marker indicating the presence or absence of the condition of interest.

When the biomarker is protein the extraction is by homogenization via sonication. The protein from the sample and the noninvasive molecular control is quantified and the quantification values are compared to determine that requisite levels of protein are present to further analyze. The protein from the sample and noninvasive molecular control is then quantified, via a protein quantification method, such as ELISA, to determine the presence or absence of the control marker indicating the presence or absence of the condition of interest.

For example, when the condition of interest is pregnancy and the control marker is cfDNA, the cfDNA is extracted from the sample and from the noninvasive molecular control simultaneously via a commercial kit that may utilize a column elution protocol with a silica-based membrane for binding, such as QIAGEN circulating nucleic acid isolation kit. Then a portion of the extracted cfDNA from the sample and from the noninvasive molecular control is used to quantify the control marker using real time PCR or digital PCR. The presence of the condition of interest will present results where the noninvasive molecular control shows an indicated percentage of the control marker (e.g. if the noninvasive molecular control contains 10% control marker, the result will show a quantative amount of approximately 10% control marker) and the sample shows a threshold (e.g. an amount of the control sample that indicates the sample has the control marker present), such as greater than 5%, of the control marker, and upon DNA sequencing, or other genetic sequence detection method, of the sample and the noninvasive molecular control both display the control marker for the condition of interest.

For example, when the condition of interest is pregnancy and the control marker is mRNA, the mRNA is extracted from the sample and from the noninvasive molecular control simultaneously via a commercial kit that may utilize a column elution protocol with a cellulose-based membrane for binding. Then a portion of the extracted mRNA from the sample and from the noninvasive molecular control is used to quantify the control marker using reverse transcriptase ddPCR or reverse transcriptase PCR. The presence of the condition of interest will present results where the noninvasive molecular control shows an indicated percentage of the control marker (e.g. if the noninvasive molecular control contains a concentration of 250 copies/mL of the control marker, the result will show a quantative concentration of 250 copies/mL of control marker) and the sample shows a threshold (e.g. an amount of the control sample that indicates the sample has the control marker present), such as a concentration greater than 250 copies/mL of the control marker, and upon mRNA sequencing, or other genetic sequence detection method, of the sample and the noninvasive molecular control both display the control marker for the condition of interest.

For example, when the condition of interest is pregnancy and the control marker is protein, the protein is extracted from the sample and from the noninvasive molecular control simultaneously by homogenization via sonication. Then a portion of the extracted protein from the sample and from the noninvasive molecular control is used to quantify the control marker by ELISA. The presence of the condition of interest will present results where the noninvasive molecular control shows an indicated percentage of the control marker (e.g. if the noninvasive molecular control contains a concentration of 0.15 micrograms/mL of control marker, the result will show a quantitative concentration of approximately 0.15 micrograms/mL and the sample shows a threshold (e.g. an amount of the control sample that indicates the sample has the control marker present), such as greater than a concentration of 0.15 micrograms/mL of the control marker, and upon ELISA or other detection method, of the sample and the noninvasive molecular control both display the control marker for the condition of interest.

When the condition of interest is Trisomy 21 and cfDNA is the control marker, the cfDNA is extracted from the sample and from the noninvasive molecular control simultaneously via a commercial kit that may utilize a column elution protocol with a silica-based membrane for binding, such as QIAGEN circulating nucleic acid isolation kit. Then a portion of the extracted cfDNA from the sample and from the noninvasive molecular control is used to quantify the control marker using real time PCR or digital PCR. The presence of the condition of interest will present results where the noninvasive molecular control shows an indicated percentage of the secondary control marker (e.g. if the noninvasive molecular control contains 10% of the secondary control marker, the result will show a quantative amount of approximately 10% of the secondary control marker) and the sample shows a threshold (e.g. an amount of the control sample that indicates the sample has the control marker present), such as greater than 5%, of the control marker, and upon DNA sequencing, or other genetic sequence detection method, of the sample and the noninvasive molecular control both display the control marker for the condition of interest.

When the condition of interest is Trisomy 21 and mRNA is the control marker, the mRNA is extracted from the sample and from the noninvasive molecular control simultaneously via a commercial kit that may utilize a column elution protocol with a cellulose-based membrane for binding. Then a portion of the extracted mRNA from the sample and from the noninvasive molecular control is used to quantify the control marker using reverse transcriptase real time PCR or reverse transcriptase ddPCR. The presence of the condition of interest will present results where the noninvasive molecular control shows an indicated percentage of the control marker (e.g. if the noninvasive molecular control contains 500 copies/mL of the control marker, the result will show a quantitative amount of approximately 500 copies/mL of the control marker) and the sample shows a threshold (e.g. an amount of the control sample that indicates the sample has the control marker present), such as a concentration from 500 copies/mL or greater, of the control marker, and upon mRNA sequencing, or other genetic sequence detection method, of the sample and the noninvasive molecular control both display the control marker for the condition of interest.

When the condition of interest is Trisomy 18 and protein is the control marker, the protein is extracted from the sample and from the noninvasive molecular control simultaneously by homogenization via sonication. Then a portion of the extracted protein from the sample and from the noninvasive molecular control is used to quantify the control marker using ELISA. The presence of the condition of interest will present results where the noninvasive molecular control shows an indicated percentage of the control marker (e.g. if the noninvasive molecular control contains a concentration of 0.15 micrograms/mL of control marker, the result will show a quantitative concentration of approximately 0.15 micrograms/mL and the sample shows a threshold (e.g. an amount of the control sample that indicates the sample has the control marker present), such as lower than a concentration of 0.15 micrograms/mL of the control marker, and upon ELISA analysis, or other detection method, of the sample and the noninvasive molecular control both display the control marker for the condition of interest.

When the condition of interest is colon cancer cfDNA is extracted from the sample and from the noninvasive molecular control simultaneously via a commercial kit that may utilize a column elution protocol with a silica-based membrane for binding, such as QIAGEN circulating nucleic acid isolation kit. The extracted cfDNA from the sample and the noninvasive molecular control is then quantified and analyzed for the control marker (e. g. KRAS G13D mutation) using real time PCR, digital PCR, or ice-COLD-PCR. The presence of the condition of interest will present results where the noninvasive molecular control shows an indicated percentage of the control marker (e.g. if the noninvasive molecular control contains 10% control marker, the result will show a quantitative amount of approximately 10% control marker) and the sample shows a threshold (e.g. an amount of the control sample that indicates the sample has the control marker present), such as greater than 2%, of the control marker, and upon DNA sequencing, or other genetic sequence detection method, of the sample and the noninvasive molecular control both display the control marker for the condition of interest.

It is believed that the present invention and many of its attendant advantages will be understood from the foregoing description. It is also believed that it will be apparent that various changes may be made in the form, construction and arrangement of the components thereof without departing from the scope and spirit of the invention or without sacrificing all of its material advantages. The form herein before described being merely an explanatory embodiment thereof, it is the intention of the following claims to encompass and include such changes.

The invention claimed is:
1. A method of making a noninvasive molecular control for determining the presence or absence of a condition of interest, the method comprising:
predetermining a positive control for the condition of interest;
selecting a first cell line for the positive control that produces a first extracellular vesicle with a first control marker for the condition of interest;
amplifying production of the first extracellular vesicle from the selected first cell line;
isolating the first control marker from the first extracellular vesicle;
quantifying the isolated first control marker;
determining a volume of the isolated first control marker for addition to an isolated control plasma;
obtaining the isolated control plasma;
treating the isolated control plasma with a control stabilizer;
determining a volume of the isolated control plasma to add to the volume of the isolated first control marker;
combining the volume of the isolated control plasma with the volume of the isolated first control marker; and
producing the noninvasive molecular control.
2. The method of claim 1, wherein the condition of interest is pregnancy.
3. The method of claim 2, wherein the selected first cell line is Tov 21 G.
4. The method of claim 2, wherein the selected first cell line is JAR.
5. The method of claim 2, wherein the selected first cell line is JAR, and wherein the first control marker is metalloprotease protein 12 placental protein.
6. The method of claim 1, wherein the condition of interest is trisomy 21.
7. The method of claim 6, wherein the selected first cell line is Detroit 532.
8. The method of claim 1, wherein the control stabilizer comprises 2-bromo-2-nitropropane-1,3-diol.
9. The method of claim 1, wherein the condition of interest is Trisomy 18.
10. The method of claim 9, wherein the selected first cell line is JAR, and where the first control marker is metalloprotease protein 12 placental protein.
11. The method of claim 1, further comprising:
selecting a second cell line for the positive control that produces a second extracellular vesicle with a secondary control marker for the condition of interest;
amplifying the production of a second extracellular vesicle from the selected second cell line;
isolating the second control marker from the second extracellular vesicle;
quantifying the isolated second control marker;

determining a volume of the isolated second control marker for addition to the isolated control plasma; and combining the volume of the isolated second control marker with the volume of the isolated control plasma and the volume of the isolated first control marker; and producing the noninvasive molecular control.

12. The method of claim 1, wherein the condition of interest is colon cancer.

13. The method of claim 12, wherein the selected first cell line is HCT 116.

14. The method of claim 1, wherein amplifying the production of the first extracellular vesicle further comprises treating the first cell line with ionophore monensin with an effective concentration from 5 to 15 mM at 37 degrees Celsius in a humidified atmosphere of 5 percent carbon dioxide for at least 24 hours.

15. The method of claim 1, wherein the isolated control plasma is human blood.

16. The method of claim 1, wherein the isolated control plasma is human urine, maternal whole blood, and/or synthetic urine.

17. The method of claim 16, where the isolated control plasma is synthetic urine.

18. The method of claim 1, wherein the isolated control plasma is blood from an animal source.

19. The method of claim 1, where the control stabilizer comprises aminocaproic acid.

20. The method of claim 1, wherein the first control marker comprises DNA or RNA.

21. The method of claim 20, wherein the first control marker is DNA.

22. The method of claim 20, wherein the first control marker is RNA.

23. A method of analyzing a sample against a noninvasive molecular control to determine the presence or absence of a condition of interest, the method comprising:
  i) producing a noninvasive molecular control by:
    a) predetermining a positive control for the condition of interest;
    b) pre-selecting a first cell line for the positive control where the preselected first cell line produces a first extracellular vesicle with a first control marker for the condition of interest;
    c) amplifying production of the first extracellular vesicle from the pre-selected first cell line;
    d) isolating the first control marker from the first extracellular vesicle;
    e) quantifying the isolated first control marker;
    f) determining a volume of the isolated first control marker for addition to an isolated control plasma;
    g) obtaining the isolated control plasma;
    h) treating the isolated control plasma with a control stabilizer;
    i) determining a volume of the isolated control plasma to add to the volume of the isolated first control marker; and
    j) combining the volume of the isolated control plasma with the volume of the isolated first control marker to produce the noninvasive molecular control;
  ii) quantifying the first control marker in the sample;
  iii) quantifying the first control marker in the produced noninvasive molecular control, thereby providing a threshold comprising an indicated percentage of the first control marker in the noninvasive molecular control; and
  iv) determining the presence or absence of the condition of interest by comparing the threshold to the quantified first control marker in the sample.

24. The method of claim 23, where the determining further comprises analyzing the sample via deoxyribonucleic acid sequencing for the first control marker.

25. The method of claim 23, where the determining further comprises analyzing the sample via reverse transcriptase droplet digital polymerase chain reaction.

26. The method of claim 23, where the determining further comprises analyzing the sample via enzyme linked immunosorbent assay.

27. A method of analyzing a sample against a noninvasive molecular control to determine the presence or absence of a condition of interest, the method comprising:
  i) producing a noninvasive molecular control by:
    a) predetermining a positive control for the condition of interest;
    b) pre-selecting a first cell line for the positive control that produces extracellular vesicles with a first control marker for the condition of interest;
    c) amplifying production of extracellular vesicles from the pre-selected first cell line;
    d) isolating the first control marker from the extracellular vesicles;
    e) quantifying the isolated first control marker;
    f) determining a volume of the isolated first control marker for addition to an isolated control plasma;
    g) providing the isolated control plasma;
    h) treating the isolated control plasma with a control stabilizer;
    i) determining a volume of the isolated control plasma to add to the volume of the isolated first control marker;
    j) combining the volume of the isolated control plasma with the volume of the isolated first control marker;
    k) pre-selecting a second cell for the positive control that produces second extracellular vesicles with a secondary control marker for the condition of interest;
    l) amplifying production of the second extracellular vesicles from the pre-selected second cell line;
    m) isolating a secondary control marker from the second extracellular vesicles;
    n) quantifying the isolated secondary control marker;
    o) determining a volume of the isolated secondary control marker for addition to the isolated control plasma; and
    p) combining the volume of the isolated secondary control marker with the volume of the control plasma and the volume of the first control marker to produce the noninvasive molecular control;
  ii) quantifying the secondary control marker in the sample;
  iii) quantifying the secondary control marker in the produced noninvasive molecular control, thereby providing a threshold comprising an indicated percentage of the secondary control marker in the noninvasive molecular control; and
  iv) determining the presence or absence of the condition of interest by comparing the threshold to the quantified secondary control marker in the sample.

28. The method of claim 27, where the determining further comprises analyzing the sample via deoxyribonucleic acid sequencing for a first control.

* * * * *